United States Patent [19]

Neward

[11] Patent Number: 5,277,613
[45] Date of Patent: Jan. 11, 1994

[54] ELECTRODE JUNCTION ASSEMBLY

[76] Inventor: Theodore C. Neward, 9251 Archibald Ave., Cucamonga, Calif. 91730

[21] Appl. No.: 885,152

[22] Filed: May 18, 1992

[51] Int. Cl.$^5$ .................................................. H01R 4/48
[52] U.S. Cl. .................................... 439/729; 439/909; 128/642
[58] Field of Search ............... 439/268, 269.1, 729, 439/819, 822, 835, 909; 128/642, 784

[56] References Cited

U.S. PATENT DOCUMENTS

| | | | |
|---|---|---|---|
| 2,528,121 | 10/1950 | Dickinson | 439/269.1 |
| 3,382,478 | 5/1968 | Satterthwait | 439/729 X |
| 4,253,721 | 3/1981 | Kaufman | 439/909 X |
| 5,046,965 | 9/1991 | Neese et al. | 439/729 X |

Primary Examiner—Larry I. Schwartz
Assistant Examiner—Khiem Nguyen
Attorney, Agent, or Firm—Lyon & Lyon

[57] ABSTRACT

There is disclosed herein an electrical junction block particularly for use with a fetal electrode and electronic monitor. The junction block comprises a housing having a cavity therein, and a substantially U-shaped spring disposed in the cavity. The spring has legs which are biased outwardly by a suitable coil spring. The housing contain electrical contacts and wires connected thereto, and the U-shaped spring can be depressed to provide openings for receiving electrode wires. A mounting pad can be disposed on the housing for facilitating mounting of the assembly on a person during use.

9 Claims, 2 Drawing Sheets

5,277,613

ELECTRODE JUNCTION ASSEMBLY

The present invention relates to electrical junctions and connectors, and more particularly to an electrode junction assembly for use with medical electrodes such as fetal monitoring electrodes.

BACKGROUND OF THE INVENTION

Monitoring fetal heartbeat by means of an electrode attached to the fetus during labor has proved to be of substantial importance in connection with childbirth. Examples of electrodes are of the type shown in Neward U.S. Pat. No. 3,910,271, Neward U.S. Pat. No. 4,254,764, and pending application Ser. No. 654,268 filed Feb. 11, 1991.

In use, the fetal electrode is attached to the head of the fetus, and electrical conductors extending from the electrode are connected to an electronic fetal heart monitor. The presently used connection is through a junction block which typically includes a pair of screw connectors. Each of the several electrode wires (two or three) is individually pushed into a connector, and a screw or threaded member is rotated to secure, both mechanically and electrically, the wire to the junction block. The junction block then typically is fastened by a suitable strap (e.g., a Velcro strap) to the leg of the woman in labor. Completing the connections is a rather cumbersome process and requires both hands. The presently used junction block typically is cleaned and disinfected so that it can be reused, but this is difficult to accomplish because of the numerous parts, threaded connectors, and the like. It would be desirable to have a simpler to use and disposable form of connector, but none has been provided even though such fetal monitoring electrodes have been in use for well over fifteen years.

SUMMARY OF THE INVENTION

The present invention is directed to a relatively simple electrode junction assembly, particularly for use with fetal monitoring electrodes during childbirth, and which enables the electrical conductors of the electrode to be relatively easily and positively inserted and connected, both physically and electrically, in a simple manner through a squeezing action. Furthermore, the assembly can be attached to an adhesive-backed pad which can be secured to the leg, abdomen, or the like of the woman during labor in the fetal monitoring process. Most of the electrode junction assembly can be simply molded, and the entire assembly can be disposed of after use.

Accordingly, it is a principal object of the present invention to provide an improved electrode junction assembly.

Another object of this invention is to provide an electrode junction assembly for a fetal electrode which is simple to use and attach.

A further object of this invention is to provide a fetal monitoring electrode junction assembly which is relatively simple in construction and can be disposable.

These and other objects and features of the present invention will become better understood through a consideration of the following description taken in conjunction with the drawings in which.

DETAILED DESCRIPTION

Figure 1:
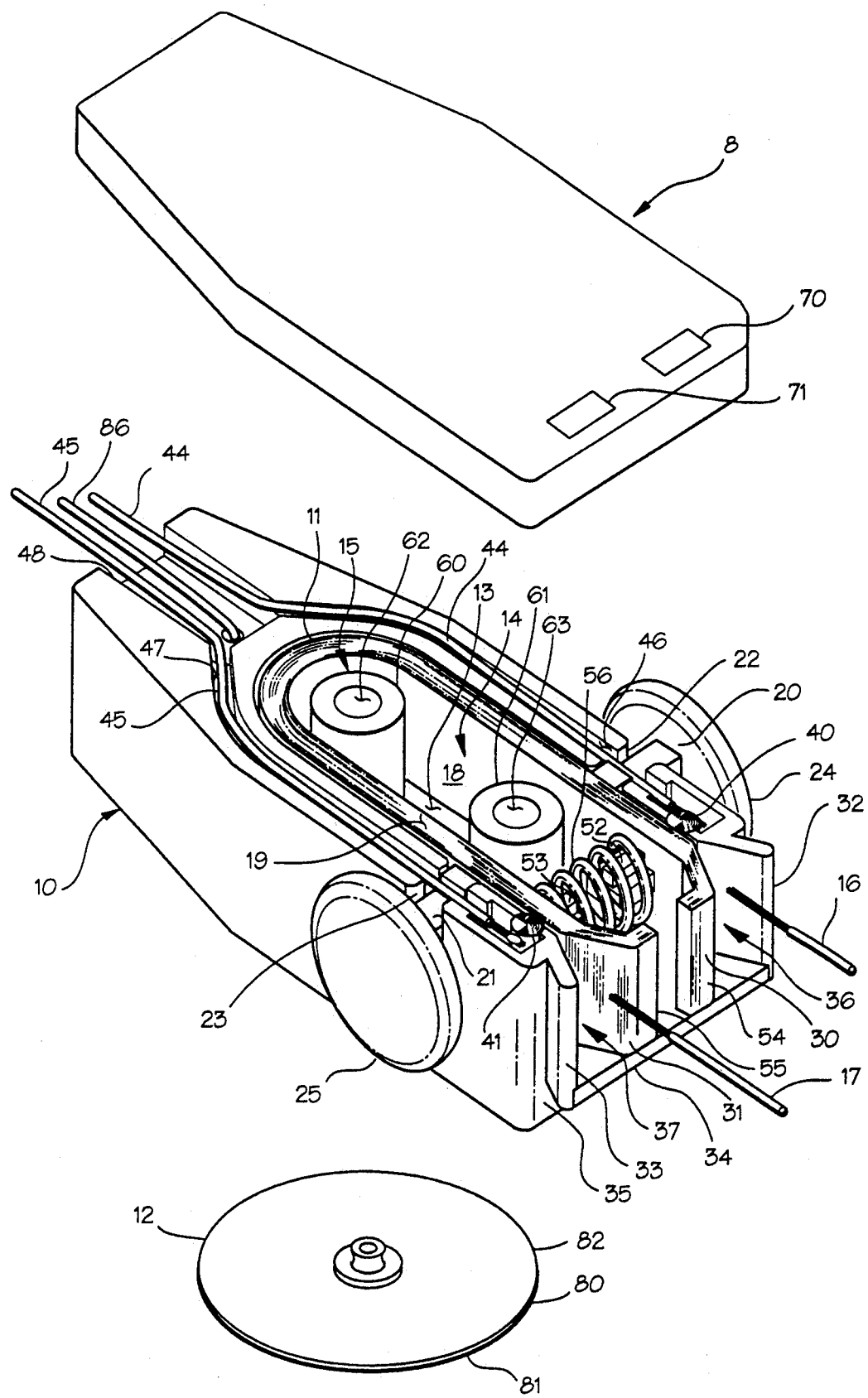
FIG. 1 is an exploded view of an electrode junction assembly according to an exemplary embodiment of the present invention comprising a housing, cover and support pad.

Turning now to the drawings, an exemplary embodiment of an electrode junction assembly according to the present invention comprises a housing or body 10 and cover 8 for the housing. A support pad 12 also may be provided and which is attachable to the underside of the housing 10 for supporting the electrode assembly (comprising the housing 10 and cover 8) on the patient during labor.

The housing 10 has an interior wall 11 and base 13 defining an interior U-shaped cavity 15. This cavity 15 contains a U-shaped spring 14 therein which, together with the interior wall 11 of the housing 10 forms a spring contact lock for a pair of fetal electrode conductors 16 and 17. The spring 14 includes a pair of legs 18 and 19 having respective outwardly and vertically extending posts or walls 20 and 21 extending through respective apertures 22 and 23 in the wall 11, and terminating in buttons 24 and 25. A coil spring 56 is disposed between the legs 18 and 19. As will be apparent shortly, these buttons 24 and 25 can be squeezed together to allow insertion of the wires 16 and 17.

Figure 2:
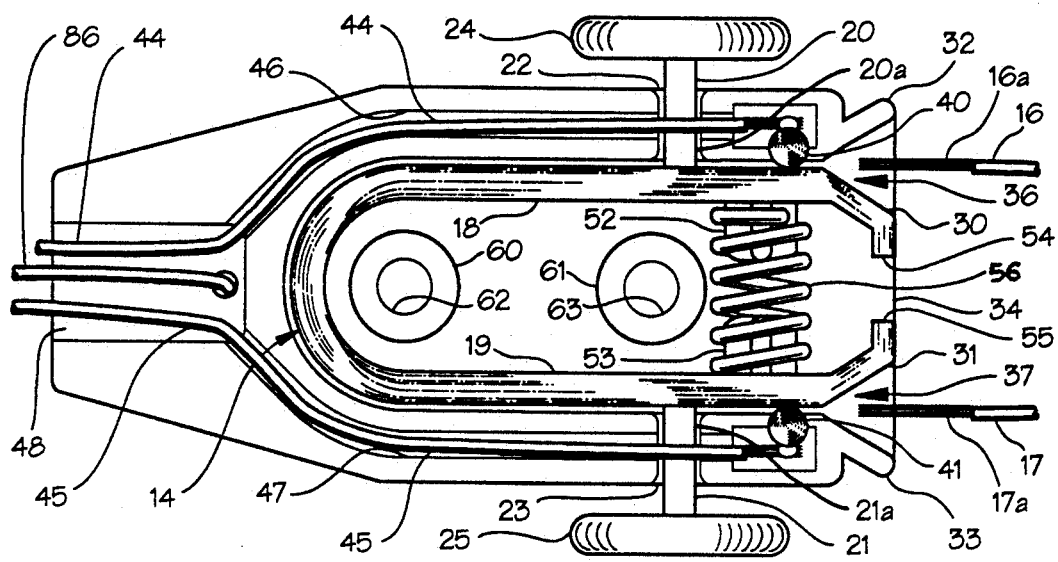
FIG. 2 is a top view of the housing of the present device with the cover removed.

The legs 18 and 19 terminate in respective inwardly turned ears 30 and 31 providing, along with outwardly turned ears 32 and 33 of the housing 10, respective guides in the shape of funnels designated by numerals 36 and 37 for tinned ends 16a and 17a of the respective electrical conductors 16 and 17 of the electrode [not shown]. A shelf 34 extending outwardly from the lower front face 35 of the housing 10 also helps ensure that the ends 16a and 17a go into the guides 36 and 37. A pair of electrical contacts 40 and 41 in the form of solid cylinders extending the height of the guide opening, are secured within the housing 10 adjacent the guide openings 36 and 37. These contacts 40 and 41 are in the form of solid cylinders and are suitably electrically connected (as by soldering) to respective electrical wires 44 and 45. These wires extend through respective cavities 46 and 47 and a cavity 48 to the exterior of the electrode block assembly for connection to an electronic fetal heart monitor (not shown) in a conventional manner. The posts 20 and 21 are essentially in the form of vertical walls and the outer faces 20a and 21a (facing to the right as seen in FIG. 2) thereof form stop surfaces for the ends 16a and 17a of conductors 16 and 17. These faces 20a and 21a thus prevent the ends 16a and 17a from being pushed in too far.

As will be apparent from the foregoing description, particularly of the spring contact 14 and housing 10, and FIGS. 1 and 2, by squeezing or pressing the buttons 24 and 25 together by, for example the thumb and index finger of one hand, the ears 30 and 31 and legs 18 and 19 move together thereby moving the outer ends of the legs 18 and 19 away from the contacts 40 and 41 to allow ready insertion of the tinned ends 16a and 17a of the electrode conductors 16 and 17. Releasing the buttons 24 and 25 allows the U-shaped spring 14 to return substantially to the position as seen in FIGS. 1 and 2, whereby the tinned ends 16a and 17a of the conductors 16 and 17 are both physically and electrically held in contact with the electrical contacts 40 and 41 by the legs 18 and 19.

The legs 18 and 19 of the U-shaped spring 14 each have a respective inwardly facing stop member 52 and 53, as well as respective protrusions 54 and 55. The legs 52 and 53 hold the coil spring 56 in position and also limit the travel of the legs 18 and 19 toward each other when the buttons 24 and 25 are pressed together. The protrusions 54 and 55 provide walls or barriers which essentially act as a shutter or blocking mechanism to prevent the wires 16 and 17 from being improperly inserted (such as between the protrusions 54 and 55) because 54 and 55 move together and abut each other when the buttons 24-25 are fully depressed. The spring 56, which may be formed of stainless steel, is mounted around the stops 52 and 53, and provides the main force to cause the legs 18 and 19 to be further biased outwardly against the electrical contacts 40 and 41 for more securely, physically and electrically, holding and entrapping the ends 16a and 17a of the conductors 16-17 against the respective contacts 40 and 41. The strength of the spring 56 can be selected to ensure that a good contact is provided between conductors 16a-17a and the contacts 40 and 41.

The base 13 may include a pair of upstanding posts 60 and 61, with holes 62 and 63, and the holes 62 and 63 receive similarly shaped posts 64 and 65 extending downwardly from the underside of the cover 8. The posts of the cover 8 are inserted in the holes 62 and 63 to secure together the cover 8 and housing 10. The cover can have markings, color coding, or the like 70 and 71 to indicate the appropriate openings 36 and 37 for the respective conductors 16 and 17.

Figure 3:
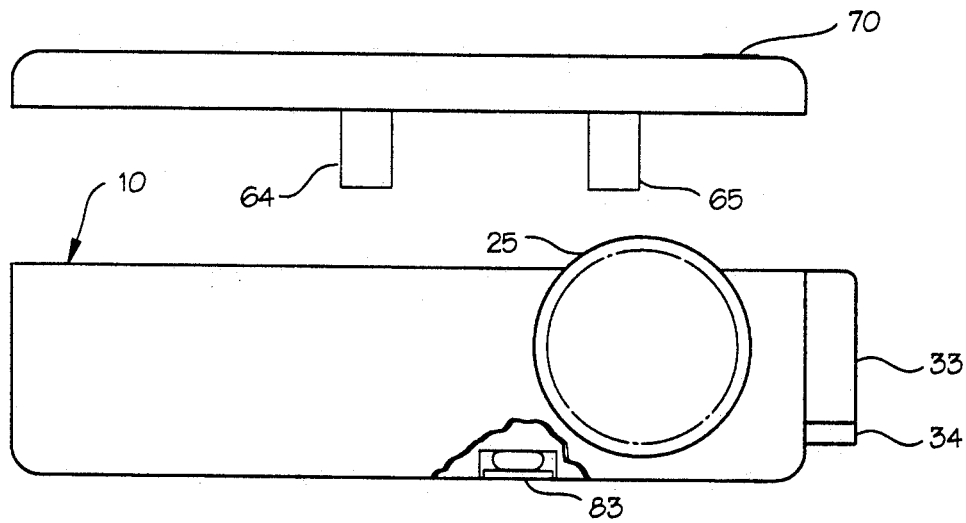
FIG. 3 is a side elevational view of the housing and cover.

The support pad 12 may comprise a resilient pad 80, such as of rubber, with adhesive 81 on the bottom surface. A snap 82, much like a clothing snap, may be provided on the pad to snap onto a mating snap 83 secured to or formed on the underside (note FIG. 3) of the housing 10. Preferably these snaps 82 and 83 allow the housing 10 to swivel on the pad 12 to minimize binding of wires. If desired, the pad 12 can be electrically conductive to provide a reference electrode as is known in the art to facilitate differentiating between the fetal heartbeat and the mother's heartbeat. In this case, the snap 82 and mating snap 83 are electrically conductive, and a third electrical conductor (not shown) is provided in the housing 10 and extends from the assembly as indicated at 86 to the electronic fetal heart monitor.

The housing 10, cover 8, and spring 14 can be injection molded of any suitable plastic material, such as PVC. The spring preferably is formed of stainless steel. It will be appreciated that the electrode junction assembly as shown in the drawings comprises only three major plastic parts (housing 10, cover 8, and spring 14), plus the spring 56, the electrical contacts 40 and 41 and associated electrical wires 44 and 45. Although the pad 12 is optional inasmuch as the present electrode junction assembly could be secured to the patient in other ways, it is preferred because it enables a very simple and compact assembly including a leg plate to be provided.

Figure 4:
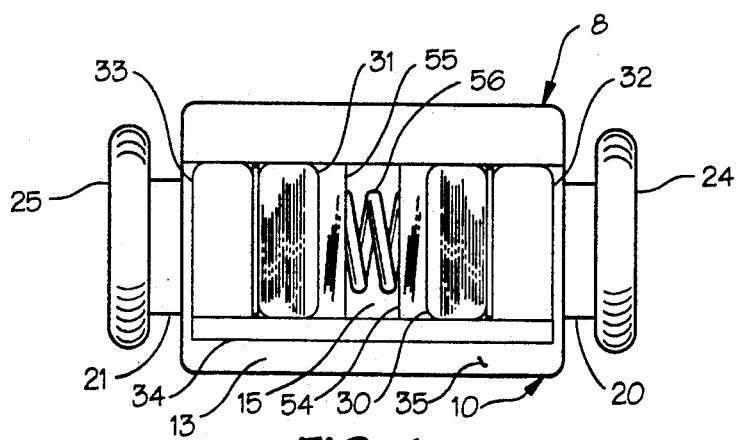
FIG. 4 is an end view of the housing and cover, which end receives the electrical conductors of the electrode.

An exemplary size for the electrode junction assembly is approximately one and one-half inches long (from left to right in FIGS. 2 and 3), about eight-tenths inch wide (from button to button as shown in FIG. 4), and approximately one-half inch high.

While an embodiment of the present invention has been shown and described, various modifications may be made without departing from the scope of the present invention, and all such modifications and equivalents are intended to be covered.

What is claimed is:

1. An electrical junction block for use with a fetal electrode and electronic monitor comprising
   a housing having sides and having a cavity therein,
   a substantially U-shaped spring disposed in the cavity, and having post members extending through the sides of the housing to enable the spring to be depressed by fingers of a person, the spring having legs terminating in angled ends disposed adjacent angled members of the housing defining therebetween a pair of guide entries for receiving the ends of electrical conductors of a fetal electrode, and
   electrical contacts connected with the housing adjacent the guide entries for electrically connecting with conductors of an electrode, and wires connecting the contacts and adapted to be connected to an electronic monitor.

2. An assembly as in claim 1 including
   a cover secured to the housing, and
   an attachment pad adapted to be connected to the housing for facilitating attachment of the assembly to a person.

3. An electrode junction block for use with a fetal electrode and electronic monitor comprising
   a housing having walls forming an interior cavity and the housing including apertures in the walls,
   a substantially U-shaped spring disposed in the cavity, the spring having legs disposed adjacent walls of the cavity for defining between each leg and a wall of the cavity a pair of guide entries for receiving the ends of electrical conductors of a fetal electrode,
   the legs including post members extending through the apertures in the walls of the housing and terminating in buttons external to sides of the housing for facilitating depression of the legs of the spring for enabling insertion of electrode conductors into the guide entries,
   electrical contacts disposed in the housing adjacent the guide entries for electrically connecting with conductors of an electrode, and wires connecting the contacts and adapted to be connected to an electronic monitor,
   the housing and U-shaped spring being molded of plastic, and
   a cover attached to the housing and covering the cavity and spring.

4. An assembly as in claim 3 wherein
   the legs of the U-shaped spring terminate in angled ends disposed against the walls of the housing, and the walls of the housing having angled members wherein the angled ends and angled members form said guide entries each substantially in the shape of the outline of a funnel.

5. An assembly as in claim 4 wherein
   the legs of the U-shaped spring include protrusions adjacent the angled ends thereof forming a shutter to block improper entry of conductors of an electrode,
   the legs of the U-shaped spring include facing fingers which form stops for limiting the degree of depression of the legs, and a coil spring is disposed on the fingers for urging the legs against the respective electrical contacts.

6. An assembly as in claim 3 wherein each leg of the U-shaped spring is acutely angled away from a respective wall, and each wall has a portion acutely angled away from a respective leg, thereby forming a guide entry substantially in the shape of a "Y" to ease entry of electrode conductors.

7. An electrical junction block for use with a fetal electrode and electronic monitor comprising a housing having sides and having a cavity therein, a substantially U-shaped spring disposed in the cavity, and having post members extending through the sides of the housing to enable the spring to be depressed by fingers of a person, the spring having legs terminating in angled ends disposed adjacent angled members of the housing defining therebetween a pair of guide entries for receiving the ends of electrical conductors of a fetal electrode, electrical contacts connected with the housing adjacent the guide entries for electrically connecting with conductors of an electrode, and wires connecting the contacts and adapted to be connected to an electronic monitor, a coil spring mounted between said legs to bias the legs toward the electrical contacts, and said post members of the spring terminate in buttons external to the sides of the housing for facilitating depression of the legs of the spring for enabling insertion of electrode conductors of an electrode, and the post members provide stops for limiting the insertion of conductors of an electrode.

8. An electrical junction block for use with a fetal electrode and electronic monitor comprising a housing having sides and having a cavity therein, a substantially U-shaped spring disposed in the cavity, and having post members extending through the sides of the housing to enable the spring to be depressed by fingers of a person, the spring having legs terminating in angled ends disposed adjacent angled members of the housing defining therebetween a pair of guide entries for receiving the ends of electrical conductors of a fetal electrode, electrical contacts connected with the housing adjacent the guide entries for electrically connecting with conductors of an electrode, and wires connecting the contacts and adapted to be connected to an electronic monitor, a cover secured to the housing, the legs of the U-shaped spring have legs facing each other to limit the degree of depression of the spring, the legs of the U-shaped spring have facing protrusions adjacent the angled ends thereof to minimize improper insertion of conductors of an electrode, and the housing, U-shaped spring and cover are molded of plastic material.

9. An assembly as in claim 8 including a pad rotatably attachable to the housing for facilitating mounting the junction block on a person.

* * * * *